United States Patent [19]

Parusel et al.

[11] Patent Number: 5,378,400
[45] Date of Patent: Jan. 3, 1995

[54] PREPARATION OF METAL OXIDE SOLS BY ELECTROLYSIS

[75] Inventors: Manfred Parusel, Munster; Klaus Ambrosius, Dieter; Klaus-Dieter Franz, Kelkheim; Wolfgang Hechler, Lautertal/Reichenbach; Matthias Schraml-Marth, Zwingenberg, all of Germany

[73] Assignee: Merck Patent Gesellschaft mit beschrankter Haftung, Darmstadt, Germany

[21] Appl. No.: 983,358

[22] Filed: Nov. 30, 1992

[30] Foreign Application Priority Data

Nov. 30, 1991 [DE] Germany .............................. 4139579

[51] Int. Cl.⁶ .................................................. C25B 1/00
[52] U.S. Cl. ................................... 252/315.01; 204/96
[58] Field of Search ............................ 204/96; 501/12; 252/315.01, 315.7

[56] References Cited

U.S. PATENT DOCUMENTS 4,801,399  1/1989  Clark et al. ................... 252/315.01

FOREIGN PATENT DOCUMENTS 715643A  2/1980  U.S.S.R. .

OTHER PUBLICATIONS

Sharygin et al. "Preparation of Aqueous Sols of Hydrated Zirconium, Titanium, and Tin Oxides by Electrolysis of Their Chlorides" pp. 670–674, pub. by Plenum Publishing Corp., 1982, month unavailable.

Primary Examiner—John Niebling
Assistant Examiner—Brendan Mee
Attorney, Agent, or Firm—Millen, White, Zelano & Branigan

[57] ABSTRACT

The invention relates to the preparation of single-multi-component metal oxide sols by hydrolysis of an aqueous metal salt solution or a solution of a metal salt mixture by direct electrolysis at −20° to 50° C.

8 Claims, No Drawings

PREPARATION OF METAL OXIDE SOLS BY ELECTROLYSIS

BACKGROUND OF THE INVENTION

The invention relates to the preparation of single- or multi-component metal oxide sols from aqueous metal salt solutions or a solution of a metal salt mixture by electrolysis.

Processes for the preparation of metal oxide sols have frequently been described in the literature. In most cases, the sols are prepared by preparing an aqueous solution of a metal salt, which is then converted into the sol state by, for example, hydrolysis, which can be effected by heating, and/or by acid peptization and/or by addition of a base. The disadvantage of these processes is that often precipitations take place instead of the sol formation, which is a great disadvantage in particular when expensive metal salts are used, for example organometallic complexes. Accordingly, the use of metal salts during salt preparation is frequently limited to low concentrations.

An improved process for the preparation of the colloids operates with ion exchangers. However, the disadvantage of this process is the limited exchanging capacity and the low reactor volume. After completion of each process, the ion exchanger needs to be replaced and regenerated, so that the process can only proceed batchwise.

Metal sols can also be obtained by electrodialysis, in which, however, sol formation and precipitations frequently compete with one another.

Electrolytic processes for the preparation of colloidal titanium salt and tin salt solutions have already been disclosed in SU 706468 and SU 929741 A and in Kolloidn. Zh. 43 (4), 192–5 and 8 12–16.

However, the preparation of a titanium oxide sol by electrolysis of a $TiCl_4$ solution can only be achieved in the presence of a stabilizing additive, such as, for example, $ZrCl_4$. During electrolysis of the pure metal salt solution, decompositions and precipitations during sol formation were increasingly observed. In the electrolytic processes described in the literature, electrolytic units comprising three chambers are used, which is complicated and requires the use of ion exchange membranes.

Multi-component metal oxide sols can be prepared in high purity and at low temperatures by hydrolysis of metal alkoxide mixtures. A disadvantage of this method is the very high price of the metal alkoxides. Accordingly, there was a need to find a simple and relatively uncomplicated process in which stable single- or multi-component metal oxide sols can be prepared in high yields without the addition of stabilizing additives.

SUMMARY OF THE INVENTION

Surprisingly, a process for the preparation of single- or multi-component metal oxide sols has now been found in which the disadvantages mentioned of conventional processes do not occur or only to a small extent.

Accordingly, the invention relates to a process for the preparation of single- or multi-component metal oxide sols, characterized in that an aqueous metal salt solution or the solution of a metal salt mixture is hydrolyzed by direct electrolysis at −20 to at most 50° C.

The metal salts used are preferably titanium compounds, aluminium compounds, zirconium compounds, hafnium compounds, niobium compounds, tantalum compounds, yttrium compounds, lanthanum compounds, actinide compounds and/or lanthanide compounds.

The single- or multi-component metal oxide sols are prepared in a simple manner by dissolving a metal salt or a metal salt mixture in water and electrolyzing the solution for several hours, while preferably recirculating the aqueous metal salt solution continuously through the electrolytic cell. The sol formation process takes place even at low temperatures. The temperature range is −20 to 50° C., preferably 0–15° C.

When the single- or multi-component metal oxide sols according to the invention are prepared, the disadvantages mentioned in the prior art do not occur or only to a limited extent, particularly where the electrolytic apparatus selected a) avoids inhomogeneities in the solution by recirculation, stirring or passing air through the solution, and b) prevents an increase in temperature by cooling.

In the sol preparation, the electrode material also plays a role. Suitable electrode materials are preferably titanium metal grate electrodes coated with ruthenium oxide or iridium oxide.

Any known metal salts which are virtually non-reducible at the cathode, i.e. which have a more positive electrode potential under the reaction conditions than the system $H_2/H^+$ at this electrode, are suitable for the process. Preferably, the oxide halides and halides of the metals, in particular the chlorides, are used. Solutions of metal salt mixtures comprising two or more different metal salts can also be converted into homogeneously mixed metal oxide sols by the process according to the invention. The electrolysis of aqueous solutions containing a maximum of three different metal salts is preferred.

Zirconium/titanium, zirconium/aluminium, zirconium/cerium, zirconium/yttrium, zirconium/cerium/lanthanum and titanium/aluminium salt solutions are particularly suitable for the electrolysis of mixtures of aqueous metal salt solutions.

Multi-component metal oxide sols can also be prepared by mixing two or more separately prepared single-component metal oxide sols. The latter, however, is a very labor- and cost-intensive method.

In the preparation of multi-component metal oxide sols by electrolysis of two or more different metal salt solutions, heteropolar bonds, i.e. for example Zr—O—Ti bonds, are already present in the sol particles, which are approximately 20 run in size, which is not the case in mixtures comprising different single-component metal oxide sols containing, for example, Zr—O—Zr and Ti—O—Ti bonds.

In the process according to the invention, there are no concentration limits with respect to the metal salt solution to be used. Usually, the reaction is carried out in the concentration range between 0.5–40% by weight, relative to the metal oxide formed.

Accordingly, the invention also relates to the use of the metal salt solution or a solution of a metal salt mixture in a concentration of 0.5–40% by weight, relative to the metal oxide formed.

Current intensity, voltage and duration of the electrolysis can vary. The voltage applied per electrolytic cell is between 2 V (decomposition voltage of water) and 20 V, preferably between 5 and 10 V. The resulting current density is in the range from 0.01 to 0.5 A/cm$^2$ and drops continuously during the electrolytic process.

Accordingly, the invention also relates to operating during electrolysis at voltages of between 2–20 V and a current intensity of between 0.01–0.5 A/cm$^2$.

The duration of electrolysis depends on the ratio of the amount of metal salt and the current intensity; for example, the conversion of 1 l of TiCl$_4$ solution containing about 350 g of TiCl$_4$/l at an anode or cathode area of 100 cm$^2$ each (initial intensity 15 A at constant voltage of 5 V) requires 25–30 h. Appropriate reaction conditions can be determined by the use of ordinary skill in the art with merely routine experimentation.

The process according to the invention proceeds according to the following equations:

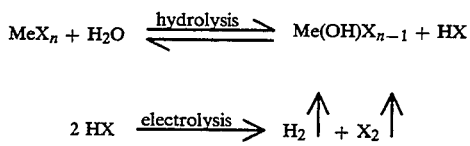

Me = metal(s)
X = customary anions.

The metal oxide sols obtained according to the invention are distinguished by their high transparency and their particle size. The sol particles have an average particle size of between 5 and 1000 nm, in particular of between 10 and 100 nm.

The concentrations of the sols depend on the concentration used of the salt solution and amount to 0.5–40% of metal oxide.

Surprisingly, it has been found that no stabilization by means of additives is necessary in the process according to the invention; this is probably due to the almost complete absence of interfering influences, such as, for example, additional membranes, differences in concentration and high temperatures.

Accordingly, the metal oxide sols are highly suitable, owing to their high transparency and variable concentration, in particular, as far as approved, for cosmetic preparations and in ceramics as lustre glaze and decorations. The TiO$_2$ sols prepared according to the invention serve in particular in cosmetics as UV protection. Titanium dioxide sols are used in ceramics, since titanium dioxide layers produced therefrom give particularly brilliant and aesthetically impressive interference colors owing to their high refractive index. The use of sols in ceramics is described, for example, in DE 41 05 235 and in cosmetics, for example, in DE 41 19 719.

Multi-component metal oxide sols can readily be converted by processes such as spray, freeze or microwave drying into amorphous powders from which polycrystalline mixed oxide powders of variable composition can be obtained by calcining at suitable temperatures.

Mixed metal oxides of this type are preferably employed as catalysts, as support materials for catalytic substances, in ceramics (e.g. zirconium titanate (ZrTiO$_4$), aluminium titanate (AlTiO$_5$), cerium- or yttrium-stabilised ZrO$_2$) and in chromatography.

Accordingly, the invention also relates to preparations containing the single- or multi-component metal oxide sols prepared according to the invention.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

The entire disclosure of all applications, patents and publications, cited above, and of corresponding German application P 41 39 579.4, are hereby incorporated by reference.

EXAMPLES

Example 1

In a glass flask fitted with double jacket and equipped with thermometer and pH electrode, 1 l of TiCl$_4$ solution (290 g of TiCl$_4$ dissolved in 1 l of water) are cooled to 10° C. This solution is continuously circulated through an electrolytic cell. After applying a voltage of 5 V and a current density of 15 A/dm$^2$, electrolysis is carried out for 30 hours, during which the current density drops to 1 A/dm$^2$. The pH of the titanium oxide sol obtained is 1.8. The sol is a water-clear, viscous liquid.

Example 2

Analogously to Example 1, 1 l of AlCl$_3$ solution (284 g of AlCl$_3$ dissolved in 1 l of water) is electrolyzed at 20° C., an initial voltage of 15 V and a current density of 7 A/dm$^2$ for 25 hours. During the sol formation process, the current density drops to 0.3 A/m$^2$. The pH of the colorless, clear viscous liquid obtained is 3.0.

Example 3

In the apparatus described in Example 1, 1 l of ZrOCl$_2$ solution (260 g of ZrO$_2$. 8 H$_2$O dissolved in 1 l of water) is cooled to 5° C. After applying a voltage of 5 V and a current density of 6.5 A/dm$^2$ electrolysis is carried out for 20 h. The final current density is 0.2 A/dm$^2$. The pH of the colorless clear sol obtained is 2.6.

Example 4

Analogously to Example 1, a ZrOCl$_2$/TiCl$_4$ solution (158.2 g of ZrOCl$_2$. 8 H$_2$O and 262 ml of TiCl$_4$ solution (357g of TiCl$_4$ dissolved in 1 l of water) in 1 l of water) is electrolyzed at 5° C., an initial voltage of 5 V and a current density of 13.7 A/dm$^2$ for 18 h, during which sol formation process the: current density drops to 1 A/dm$^2$.

The water-clear zirconium titanate sol obtained can be converted into a white pourable powder by the known drying processes.

Comparison Example

Equimolar amounts of the titanium oxide and zirconium oxide sols prepared separately in Example 1 and Example 3 are mixed and the mechanical mixture is then dried.

Analogously to Example 4, crystalline zirconium titanate is formed from 400° C. upwards.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of single-or multi-component metal oxide sols, comprising hydrolyzing an aqueous metal salt solution or a solution of a metal salt mixture by direct electrolysis at 0° to 15° C., wherein the metal salt solution is without stabilizing additive and is continuously recirculated through an electrolytic cell.

2. A process according to claim 1, wherein air is passed through the solution.

3. A process according to claim 2, wherein the metal salt is an aluminum compound, a titanium compound, a zirconium compound, a niobium compound, a tantalum compound, a yttrium compound, an actinide compound or a lanthanide compound.

4. A process according to claim 2, wherein during electrolysis a voltage of between 2-20 V and a current intensity of between 0.01-0.5 A/cm$^2$ are applied.

5. A process according to claim 2, wherein the metal salt solution or a solution of a metal salt mixture is used in a concentration of 0.5-40% by weight, relative to the metal oxide or metal oxide mixture formed.

6. A single- or multi-component metal oxide sol prepared by the process according to claim 2, having a particle size of 5-1,0000 nm.

7. A single- or multi-component metal oxide sol prepared by the process according to claim 2, having a particle size of 10-100 nm.

8. A process for the preparation of single- or multi-component metal oxide sols, comprising hydrolyzing a solution consisting of at least one aqueous metal salt, by direct electrolysis at 0° to 15° C., wherein the solution is continuously recirculated through an electrolytic cell.

* * * * *